(12) United States Patent
Kathe et al.

(10) Patent No.: US 9,897,549 B2
(45) Date of Patent: Feb. 20, 2018

(54) ANALYTICAL DEVICE FOR AUTOMATED DETERMINATION OF A MEASURED VARIABLE OF A LIQUID SAMPLE

(75) Inventors: Ulrich Kathe, Ludwigsburg (DE); Ralf Steuerwald, Eberdingen (DE); Thomas Schipolowski, Stuttgart (DE); Matthias Knopp, Weissach-Flacht (DE); Tobias Zachmann, Stuttgart (DE); Thomas Baumgartner, Stuttgart (DE)

(73) Assignee: Endress+Hauser Conducta GmbH+Co. KG, Gerlingen (DE)

( * ) Notice: Subject to any disclaimer, the term of this patent is extended or adjusted under 35 U.S.C. 154(b) by 1387 days.

(21) Appl. No.: 13/426,757

(22) Filed: Mar. 22, 2012

(65) Prior Publication Data

US 2012/0258542 A1    Oct. 11, 2012

Related U.S. Application Data

(60) Provisional application No. 61/457,756, filed on May 27, 2011.

(30) Foreign Application Priority Data

Apr. 7, 2011    (DE) .................. 10 2011 007 011

(51) Int. Cl.
  *G01N 21/11*    (2006.01)
  *G01N 35/00*    (2006.01)
  (Continued)

(52) U.S. Cl.
  CPC ............ *G01N 21/78* (2013.01); *G01N 21/11* (2013.01); *G01N 35/1002* (2013.01);
  (Continued)

(58) Field of Classification Search
  None
  See application file for complete search history.

(56) References Cited

U.S. PATENT DOCUMENTS 4,515,753 A * 5/1985 Smith .................. B01L 3/0293
                                                          206/219
5,800,056 A    9/1998 Suzuki
(Continued)

FOREIGN PATENT DOCUMENTS

CN    1749757 A    3/2006
DE    69125343 T2    7/1997
(Continued)

OTHER PUBLICATIONS

Search Report issued by German Patent and Trade Mark Office for DE 102011007011.7, dated Jan. 25, 2012, 4 pages.

*Primary Examiner* — Yelena G Gakh
*Assistant Examiner* — Michelle Adams
(74) *Attorney, Agent, or Firm* — Christopher R. Powers; PatServe (57) ABSTRACT

An analytical device, including: a processing system for treating a liquid sample and for supplying the treated liquid sample to a measuring cell, to the liquid sample; a measuring transducer for registering a measured value of the treated liquid sample variable; a control unit to control the processing system; and an evaluating unit for determining the measured variable based on the measured value registered by the measuring transducer. The analytical device includes at least one first supply container containing a first reagent component, at least one second supply container containing a second reagent component and a mixing apparatus, for mixing a predetermined amount of the first reagent component contained in the first supply container with a predetermined amount of the second reagent component to form a predetermined amount of the reagent.

18 Claims, 3 Drawing Sheets

(51) Int. Cl.
    *G01N 21/78*     (2006.01)
    *G01N 35/10*     (2006.01)
(52) U.S. Cl.
    CPC .. *G01N 35/1095* (2013.01); *B01F 2215/0037* (2013.01); *G01N 2035/1058* (2013.01); *Y10T 436/11* (2015.01)

(56) References Cited

U.S. PATENT DOCUMENTS

| | | | |
|---|---|---|---|
| 6,299,567 B1* | 10/2001 | Forrest et al. | 482/64 |
| 2004/0115829 A1* | 6/2004 | Kaartinen et al. | 436/180 |
| 2005/0214165 A1* | 9/2005 | Babel et al. | 422/63 |
| 2006/0030049 A1* | 2/2006 | Bhimani et al. | 436/43 |
| 2010/0248289 A1* | 9/2010 | Asahara | G01N 35/00663 435/29 |
| 2012/0173164 A1 | 7/2012 | Steuerwald et al. | |

FOREIGN PATENT DOCUMENTS

| | | |
|---|---|---|
| DE | 19821903 A1 | 1/1999 |
| DE | 10227032 A1 | 11/2003 |
| DE | 10222822 A1 | 12/2003 |
| DE | 10 2009029305 A1 | 3/2011 |
| WO | WO 2006/063789 A1 | 6/2006 |

* cited by examiner

ANALYTICAL DEVICE FOR AUTOMATED DETERMINATION OF A MEASURED VARIABLE OF A LIQUID SAMPLE

CROSS-REFERENCE TO RELATED APPLICATION

This application is a nonprovisional which claims the benefit of U.S. Provisional Application 61/457,756, which was filed on May 27, 2011.

TECHNICAL FIELD

The invention relates to an analytical device for automated determination of a measured variable of a liquid sample.

BACKGROUND DISCUSSION

Such analytical devices are applied, for example, in process measurements technology or in industrial measurements technology. For example, analytical devices can serve to monitor and optimize the cleaning effectiveness of a clarification plant, to monitor an aeration basin and the outlet of a clarification plant or to control a flocculent. Furthermore, analytical devices can be applied to monitor drinking water or to monitor the quality of food. The content of specific substances, for example, ions such as ammonium, phosphate, silicate or nitrate, or biological or biochemical compounds, e.g. hormones, or also microorganisms in the liquid sample is measured and monitored. The total carbon content (TOC) or the chemical oxygen demand (COD) are other measured variables, which are determined by analytical devices in process measurements technology, especially in the area of water monitoring.

In analytical devices, the sample to be analyzed is frequently mixed with one or more reagents, so that a chemical reaction occurs in the liquid sample. Preferably, the reagents are selected so that the chemical reaction is detectable by means of physical methods, for example, through optical measurements or by means of potentiometric or amperometric sensors or through a conductivity measurement. For example, the chemical reaction can affect a coloring or a color change, which is detectable photometrically, thus through optical means. In this case, the color intensity is dependent on the value of the measured variable to be determined.

In order to automate such analytical methods, for example, in industry, or to monitor a clarification plant or a body of water outdoors, the provision of an automated analytical device, which performs the required analytical method, is required. In addition to a sufficient accuracy of measurement, the most important requirements for such an analytical device are robustness, easy serviceability and the assurance of a sufficient working or environmental safety.

Semi-automatic and automatic analytical devices are known from the state of the art. Thus, for example, DE 102 22 822 A1, DE 102 20 829 A1 and DE 10 2009 029305 A1 describe online analyzers for analyzing measurement samples. Each online analyzer is embodied as cabinet device including a control unit, a liquid supply container for reagents, standards and cleaning liquids, pumps for conveying and dosing the liquid sample and or reagent(s) into a cuvette and a measuring transducer for optical measurements of the liquid sample mixed with the reagent(s) in the cuvette. The reagents are moved through lines from the supply containers into the cuvette. Correspondingly, used liquid from the cuvette is transferred to the waste liquids container.

The liquid supply containers of such an analytical device must be refilled or replaced from time to time. In many analytical methods, liquids, which have only a limited storage life, are used as reagents. The time span, also referred to as the maintenance interval, after which a replacement or a refilling of at least the liquid supply containers containing reagents is required, is frequently not primarily determined by the liquid volume contained in the supply containers and the consumption of reagents by the analytical device, but rather by the limited storage life of the reagents. However, it is desirable to use such an automatic analytical device for as long a period of time as possible without maintenance measures to be performed by operators.

German Offenlegungsschrift DE 195 36 789 A1 proceeds from knowledge that storage life of reagents of an automatic analytical device is frequently reduced by gases, such as oxygen, carbon dioxide or ammonia getting into the supply container. Evaporation can also degrade the analytical results in the case of supply containers open to the atmosphere. In German Offenlegungsschrift DE 195 36 789 A1, a vessel for liquids, which limits both the ability of air to get in and the evaporation of reagents, is provided to improve the storage life of liquids contained in analyzers. The vessel includes a removal opening, starting from which a tube extends into the vessel. A gas exchange occurs between the environment and the liquid in the vessel via the tubes, which should preferably penetrate into the liquid. The size of the removal opening is selected for limiting the ability of air to get in and for the evaporation to be as small as possible.

Moreover, DE 195 36 789 A1 discloses an approach known from the state of the art for lengthening the storage life of liquids. The opening of the supply container is provided with a septum, which is penetrated by a pipetting needle in removal steps. Such an apparatus requires, however, a relatively high mechanical stability of the pipetting needle. Moreover, a pipetting needle is not robust and unsuitable for application in a cabinet device, which is to be applied for monitoring a body of water, even outside in given cases, or in a clarification plant.

It is true that both approaches for lengthening the storage life of the reagents described in DE 195 36 789 A1 bring about an improvement compared to the application of open supply vessels; however, they only lead to a slowing of the degradation of reagents; this degradation is especially caused by contact with air. The contact with air cannot be completely prevented in both cases, so a maintenance free operation of the analytical device over a period of time of many months is not possible. A continuous degradation of the reagents and therewith a continuous worsening of the quality of the analytical results is to be expected, at the least.

SUMMARY OF THE INVENTION

It is therefore an object of the invention to provide an analytical device, which overcomes the disadvantages of the state of the art. Especially, the analytical device should be able to deliver high quality analytical results over a long period of time, especially over a number of months, without requiring a service person to replace reagents, especially reagents with limited storage life, during this period of time.

This object is achieved by an analytical device for automated determination of a measured variable of a liquid sample which includes:

a processing system for treating the liquid sample and for supplying the treated liquid sample to a measuring cell, wherein treating includes adding at least one reagent to the liquid sample;

a measuring transducer for registering a measured value of the treated liquid sample contained in the measuring cell, which measured value is correlated with the measured variable;

a control unit for controlling the processing system; and an evaluating unit for determining the measured variable based on the measured value registered by the measuring transducer, wherein the analytical device includes at least one first supply container containing a first reagent component, at least one second supply container, which is separated from the first supply container at least at times and which contains a second reagent component, and a mixing apparatus, especially a mixing apparatus controllable by the control unit, for mixing a predetermined amount of the first reagent component contained in the first supply container with a predetermined amount of the second reagent component contained in the second supply container to produce a predetermined amount of the reagent.

For example, the reagent can be a pH buffer, which serves to set a certain pH value of the liquid sample. The reagent can be a decomposition reagent for the liquid sample or a masking reagent for masking interfering substances. Interfering substances are chemical substances whose presence influences the measurement signal of the measuring transducer in a manner such that the determination of the measured variable is corrupted.

The reagent can especially contain at least one chemical substance, which influences a property of the liquid sample; the property is detectable by the measuring transducer and is dependent on the measured variable of the liquid sample to be determined. If the measured variable to be determined is the concentration of an analyte, for example, an ion, such as ammonium, nitrate or phosphate, in the liquid sample, then mixing the reagent with the liquid sample can lead, due to a chemical reaction, in which the analyte and one or a number of chemical substances of the reagent participate, to produce a reaction product, which has a characteristic property, especially an optical property, for example, a characteristic absorption maximum in the visible spectral range, the near infrared range (NIR) or the ultraviolet spectral range (UV). For example, a coloring or color change of the treated liquid sample can occur; the coloring or color change can be detected through a photometric measuring of one or more wavelengths in each relevant spectral range. One or more chemical substances present in the reagent can thermally or photochemically decompose or undergo chemical reactions with one another, with air components, e.g. oxygen, or with other substances present in the environment, leading to the decomposition of the substance or substances required for determining the measured variable. A corruption of the analytical results, i.e. the results of the determination of the measured variable to be determined in the liquid sample, can result from the decline of the actual concentration of this substance or these substances in the reagent. It is, therefore, advantageous to divide the components of the reagent into two or more reagent components, each of which can comprise one or a number of individual chemical substances, which in the combination of the respective reagent components present do not undergo chemical (decomposition) reactions or only undergo very slowly acting, chemical (decomposition) reactions in the conditions present in the supply containers. Thus, these reagent components are stored in supply containers separated from one another.

The predetermined amount of the reagent can be automatically produced by mixing the first and the second reagent components, or even more reagent components in given cases, when required by the analytical device, especially controlled by the control unit. This mixing can be repeated as required. In this way, a continuous degradation of the quality of the measurement results of the analytical device can be prevented, since the best possible quality of reagent is available after each newly performed mixing. The reagent can be produced in the amount required for a single analysis directly before each analysis of the liquid sample. It is especially advantageous, however, to produce an amount of reagent sufficient for the analysis of more or many liquid samples, since in this way, on the one hand, time for mixing the reagent must not be expended before each measurement and on the other hand, however, after the analysis of a certain number of liquid samples a new amount of the reagent can still be produced before the quality of the analytical results essentially worsens. This amount of reagent sufficient for the analysis of a number of liquid samples, also referred to in the following as a charge, can be so dimensioned that the reagent, with a foreseeable consumption, is used up within its storage life during the operation of the analytical device. The length of the storage life of the reagent corresponds to the time span after producing the charge within which reliable analytical results are achieved. This time span can be ascertained based on preliminary experiments or empirical values. The predetermined amount of reagent produced for a number of analyses can be placed and stored in a mixing container provided for this.

The mixing apparatus can at least partially be a component of the processing system. The mixing apparatus can include a supply system controllable by the control unit for supplying and dosing one or more reagent components into a mixing container. One of the supply containers, in which one of the reagent components is contained, can serve as a mixing container, for example. In another embodiment the mixing apparatus can also have an additional mixing container, to which the two reagent components are conveyed and then dosed. The additional mixing container can also be only a liquid line, in which the reagent components are fed together and mixed before being added to the liquid sample. The supply system can be embodied as a pump, for example, a peristaltic pump, a membrane pump or a syringe pump. Advantageously, the same pump also serves to convey and dose the reagent for the treating of the liquid sample into one of the liquid lines that convey the liquid sample or directly into a mixing cell or into a measuring cell.

The processing system includes liquid lines, which form a flow path, via which the liquid sample supplied from a sample supply is transported into the measuring cell. The liquid sample can be subjected, for example, to one or more treatment steps along this flow path and the treated liquid sample can then be conveyed into the measuring cell. The treatment of the liquid sample can be, for example, the setting of a certain pH value of the liquid sample, a chemical decomposition or adding a reagent affecting a color change in the presence of a certain analyte. For example, a treatment cell or mixing cell can be arranged upstream from the measuring cell in the flow path; at least the treatment step of adding the reagent to the liquid sample is performed in the treatment cell or mixing cell. Alternatively, the treated liquid sample can be provided within the measuring cell, in that the liquid sample is directly conveyed, thus untreated, into the measuring cell, and the liquid sample is treated there. In this case, the measuring cell simultaneously serves as a mixing cell or treatment cell.

The processing system can furthermore include one or more supply and dosing systems, which include e.g. membrane pumps, hose pumps, peristaltic pumps or syringe pumps, and are controllable by the control unit; the supply and dosing systems convey the liquid sample, at least one reagent, or the liquid sample treated with the reagent and, in given cases, other liquids, e.g. cleaning liquids or calibration standards, into the measuring cell and/or, in given cases, into a treatment cell or mixing cell connected in the flow path upstream from the measuring cell.

Relative to the measuring cell, the measuring transducer can be arranged in such a manner that it is in contact or can be brought into contact with the treated liquid sample present in the measuring cell for registering a measured value. If the measuring transducer is, for example, an optical sensor with a radiation source, which emits measuring radiation, and a receiver, which outputs a measurement signal dependent on the radiation intensity impinging on a sensitive surface of the receiver, the measuring transducer is brought into contact with the liquid sample, in that radiation emitted by the radiation source is radiated on a radiation path extending between the radiation source and the receiver through the treated liquid sample, especially through the wall or through one or more windows of the measuring cell. If the measuring transducer is embodied as an amperometric or potentiometric sensor, e.g. an ion selective electrode, or a conductivity sensor, the measuring transducer is brought into contact with the treated liquid sample, in that a fixed immersion region of the measuring transducer for contact with the treated liquid sample is wetted by the liquid sample. For example, the measuring transducer or at least one immersion region of the measuring transducer sensitive to the measured variable can be arranged within the measuring cell for this purpose.

The registration of a measured value by the measuring transducer can be triggered by the control unit. The determination of the measured variable from the measured value occurs by means of the evaluating unit. The evaluating unit and the control unit can be formed by a data processing unit, for example, a computer or a measurement transmitter. The control unit and data processing unit can also be realized through a number of data processing units, especially spatially distributed data processing units, in connection with one another for communication. The functionality of the evaluating unit and the control unit can be especially realized through a microcomputer with one or more processors and one or more data memory circuits.

In an embodiment of the analytical device, the mixing apparatus can have means for conveying and dosing the second reagent component from the second supply container into the first supply container and for mixing the first reagent component contained in the first supply container with the predetermined amount of the second reagent component supplied to the first supply container. Thus, in this embodiment the first supply container serves as a mixing container and simultaneously as a reservoir for the newly produced charge of the reagent, from which the processing system supplies a predetermined amount of the reagent for treating a liquid sample and for the following determination of the measured variable. The means for conveying the second reagent component to the first supply container can include, for example, a pump actuatable by the control unit, especially a membrane pump, a peristaltic pump or a syringe pump, as well as one or more liquid lines, which connect the second supply container to the first supply container. If a plurality of first and/or second supply containers are present, the means for conveying the second reagent component to the first supply container preferably includes one or more valves actuatable by the control unit; the supply container from which or into which the reagent component is to be conveyed can be selected by means of the valves.

In an additional embodiment, the analytical device can have one or more additional supply containers in addition to the first supply container; each of these additional supply containers contains a predetermined amount of the first reagent component. This embodiment permits producing a number of charges of the reagent one after the other by mixing the first reagent component contained in a supply container with a predetermined amount of the second reagent component, for example, through conveying the predetermined amount of the second reagent component to one of the supply containers with the first reagent component, wherein each charge preferably is only used by the analytical device for the measurement of the measured variable until a predetermined length of storage life of the reagent has passed. The control unit is, in this case, embodied to produce a new charge after consumption of the current charge, i.e. the most recently produced charge, or after the expiration of the length of storage life of the reagent.

In this embodiment, the analytical device can also have, in addition to the second supply container, one or more additional supply containers; each of these additional supply containers contains a predetermined amount of the second reagent component. If the analytical device includes only one or at least fewer supply containers for the second reagent component than supply containers for the first reagent component, then the required amount of the second reagent component for a charge of reagent can be set for dosing the second reagent component into the supply container containing the first reagent component by means of the mixing system or by means of the supply system. This embodiment saves space, since, as a whole, fewer supply containers are required. Alternatively, however, a number of supply containers with the second reagent component equal to the number of supply containers with the first reagent component can be provided, wherein each amount contained in the supply containers is so dimensioned that the mixing ratio of the first and second reagent components required for producing the reagent is set by mixing the content of a supply container with the first reagent component and the supply of a container with the second reagent component.

For example, the control unit can be so embodied to register the time since producing the most recently produced reagent charge and produce an additional charge after the expiration of a time span. The time span can be stored in a memory of the control unit as a fixed value, especially the value associated with the length of the storage life of the reagent. The length of storage life can be derived, for example, from empirical values from the manufacturer or the user of the analytical device or from targeted preliminary tests. It is also possible to embody the control unit, so that it adjusts the time span stored in a memory to the current operating conditions based on the reagent consumption of the analytical device. Thus the time span can be correspondingly adjusted, for example, in the case of a change of the frequency with which liquid samples are removed from the sample supply and the measured variable to be monitored is determined by means of the analytical device or in the case of a change in the environmental conditions, e.g. a significant change in the ambient temperature over a longer time.

The aging of the reagent can also be monitored by sensors. Frequently, decomposition reactions are associated with a change of the measurable properties of the reagent, for example, with a discoloration, a change of the pH value or the conductivity of the reagent. Consequently, the analytical device can be embodied to monitor physical or chemical properties of the reagent that change with aging, especially with progressive deterioration, of the reagent. For example, if an increasing deterioration of the reagent leads to an increased coloring or color change of the reagent, such can be registered by means of an optical measuring transducer, especially by means of the same measuring transducer, which also serves to determine the measured variable of the liquid sample. For example, the control unit can be embodied to supplementally perform a photometric absorption measurement with a characteristic wavelength for the decomposition reaction with calibration measurements occurring between measuring cycles serving to determine the measured value, and to derive the degree of aging of the reagent therefrom. For example, a threshold value for the absorption of the characteristic wavelength can be stored in the control unit; the threshold value corresponds to a concentration of the decomposition product, where the concentration no longer assures a sufficient quality of the measured values made available to the analytical device to determine the measured variable. Upon reaching this threshold value, the control unit produces a new charge of reagent.

Alternatively or supplementally to monitoring the time span since production of each most recently produced charge, or alternatively or supplementally to the monitoring of the aging of the reagent by sensors, the amount provided in the supply containers containing the first reagent component can be so dimensioned that the charge of reagent produced therewith is sufficient until the expiration of the length of storage life with an average consumption by the analytical device. Thus, it is assured that the current charge of the reagent is, on the one hand, sufficient up to producing the next charge; on the other hand, however, the remainder of no longer usable reagent, which must be disposed of as waste, is not large.

In this embodiment, a value representing consumption of the reagent and a value representing the amount of the first reagent component contained in the supply containers can be stored in a memory of the control unit, wherein the control unit is embodied to ascertain the time span based on these values; after this time span, a predetermined amount of the second reagent component is conveyed to one of the additional supply containers in order to produce a new charge.

The second reagent component can be a liquid; the first reagent component can be a solid, especially a powder or granular material, which is soluble in the second reagent component. For example, the second reagent component can be essentially water or an organic solvent. For producing a charge of reagent by mixing the second reagent component with the first reagent component, the liquid second reagent component can be conveyed to the first supply container, which contains the solid, first reagent component, and be dosed in the amount required for a desired mixing ratio of the reagent components. A complete mixing and dissolving of the first reagent component in the second reagent component can be achieved with the assistance of a stirrer integrated in the first supply container or through one or multiple recirculations of the mixture.

The supply containers can be embodied as flexible reagent bags, each having a connection, especially a single connection, to connect the reagent bag, in each case, to one liquid line. A liquid reagent can be removed from a flexible reagent bag without having to be concerned about pressure equalization within the supply container. Thus, only a single container opening is required for the removal of liquid, namely the mentioned connection for the connection of the reagent bag to one liquid line, so that the penetration of air, especially oxygen or other reactive gases, into the supply container can be largely suppressed.

The supply containers, especially embodied as flexible reagent bags, can advantageously have a container wall impermeable to visible light and/or UV radiation. Therewith, the photochemical aging or decomposition processes, or the aging or decomposition processes accelerated by radiation, of the substances contained in the reagent components or each newly mixed reagent are at least slowed or even suppressed. In an embodiment of the supply container as a reagent bag, the container wall can be formed by a film impermeable to visible light and/or UV radiation, for example. In this context, films or coatings, which supplementally reflect IR radiation, are especially advantageous and so the contents of the bag are also thermally insulated.

In an embodiment, a temperature regulating apparatus, especially a cooling apparatus, can be associated with at least a first supply container or the multiple supply containers containing the first reagent component; the temperature regulating apparatus includes, for example, a Peltier element. In or after producing a reagent charge, e.g. through conveying the second reagent component to the first supply container, the supply container containing the reagent can be cooled in order to slow decomposition reactions and so increase the length of storage life of the reagent. With this measure, the time span until producing an additional reagent charge can be further lengthened.

If the supply containers are embodied as reagent bags, they can be arranged in the analytical device in support containers, which have a floor and fixed walls laterally surrounding the reagent bag. The temperature regulating apparatus can be arranged, for example, within the support container or integrated in at least one container wall of the support container. The container walls and the floor of the support container can have a thermal insulation, which thermally insulates the interior of the support container from the environment. For example, the container walls and the floor can have a double walled structure.

In an advantageous embodiment, the supply containers are arranged in a cartridge, which is insertable into and removable from the analytical device; the cartridge especially includes a temperature regulating system to regulate the temperature, especially to cool, at least one or all the supply containers. Support containers for reagent bags can be provided in the cartridge as in the embodiment described previously. At least one of the support containers can have a cooling apparatus, for example, a Peltier element, in its interior and/or integrated in at least one container wall of the support container for cooling reagent bags. Supplementally or alternatively a temperature regulating apparatus, especially a cooling apparatus, can be provided for regulating the temperature of the cartridge as a whole. The temperature regulating apparatuses here and in the previous embodiment are preferably controlled and/or regulated by the control unit of the analytical device. If the supply containers are integrated in a removable cartridge, the cartridge can alternatively or supplementally have a cartridge control unit in the form of a data processing system having, for example, at least one microprocessor or a microcontroller and a data storage circuit. This cartridge control unit can be embodied to control and/or regulate the temperature regulating apparatus of the cartridge or, in given cases, the temperature regulating apparatuses associated with the supply containers or support containers formed in the cartridge.

Instead of a complete data processing system, the cartridge can also have only a data memory, in which information on the reagent components contained in the supply containers are stored. For example, this information can include one or more of the following: The amount contained in each supply container, the length of storage life of the individual reagent components and/or the storage life of a reagent produced by mixing the reagent components and the amount of reagent required for determining the measured variable in a liquid sample. The data memory can also contain the time span mentioned above, after which the control unit produces an additional charge of reagent after production of the current charge of reagent. The control unit can be embodied to read out this information from the data memory and to use it to control the analytical device after the insertion of the removable cartridge in the analytical device. The control unit can also be embodied to store data in the data memory of the cartridge, for example, information concerning consumption of the liquids contained in the cartridge, especially the reagent components; the amount of reagent components and reagent still remaining in the cartridge can be determined from this data.

The invention also includes a method for determining a measured variable in a liquid to be monitored by means of an analytical device, especially an analytical device according to one of the previously described embodiments and variants, with a processing system controlled by a control unit, a measuring cell, a measuring transducer and an evaluating unit, including the following steps:

treating a liquid sample of the liquid to be monitored by means of the processing system, wherein at least one reagent is added to the liquid sample,
  supplying the treated liquid sample to the measuring cell,
  registering, by means of the measuring transducer, a measured value correlated with the measured variable of the treated liquid sample supplied to the measuring cell and transmitting the measured value to the evaluating unit,
  determining by the evaluating unit of a value of the measured variable based on the measured value registered by the measuring transducer, wherein the reagent is produced by means of a mixing apparatus of the analytical device, in that the mixing apparatus mixes a predetermined amount of a first reagent component contained in a first supply container with a predetermined amount of a second reagent component contained in a second supply container, which is at least at times separated from the first supply container.

The mixing apparatus can be controlled by the control unit. It can be a component of the processing system, as mentioned above in the description of the analytical device.

The step of treating the liquid sample can also include other method steps besides the step of adding at least one reagent. In such case, instead of just one reagent, a number of reagents can be added one after the other or simultaneously. For example, first a reagent for setting a certain pH value, for example, a buffer solution, can be added to the liquid sample; thereafter, adding an additional reagent, which serves as a detection reagent; this additional reagent reacts with analyte possibly contained in the liquid sample as a color change or by influencing another physically measurable property of the treated liquid sample.

The sequence of the said steps of treating the liquid sample, supplying the liquid sample to the measuring cell, registering a measured value correlated with the measured variable and determining a value of the measured variable is also referred to as the measuring cycle of the analytical device. Preferably, a predetermined amount of at least one reagent sufficient for performing a plurality of such measuring cycles is produced in each charge.

A charge so produced can be held in a supply container serving as a reagent reservoir, wherein the processing system supplies reagent from the reagent reservoir for adding reagent to the liquid sample. The first supply container can especially serve as a reagent reservoir when the second reagent component is conveyed to the first supply container for the mixing of both reagent components and the mixing of the components is performed in this supply container, as presented in detail above in the description of the analytical device.

In this way, a number of reagent charges can be produced one after the other. Each charge is only used for determinations of the measured variable by the analytical device as long as a predetermined length of storage life of the reagent is not exceeded. After consumption or the expiration of the predetermined length of storage life of the charge most recently produced, the control unit can initiate producing a new charge by mixing a predetermined amount of the first reagent component with a predetermined amount of the second reagent component and perform this by means of the processing system or, more specifically, the mixing system. The length of the storage life depends on the composition of the reagent and on the conditions, such as e.g. the temperature in the supply containers. The length of storage life can be lengthened through additional measures, such as e.g. cooling the supply container containing the reagent or protecting the reagent contained in the supply container from irradiation by UV or visible light. The reagent amount per charge can advantageously be dimensioned by the control unit, so that this reagent amount is essentially applied in the measuring cycles performed within the length of storage life with a foreseeable consumption rate of reagent. Thereafter a new reagent charge is produced.

A memory of the control unit can hold a value, for example, a fixedly predetermined value, correlated with the length of the storage life of the reagent. In an optional embodiment of the method, the control unit can adjust the value for the length of the storage life held in the memory, for example, based on the consumption of reagent by the analytical device or a change of operating conditions. For example, the analytical device can have one or more temperature sensors, which register(s) the temperature of the reagent and/or the ambient temperature. On the basis of the registered values of temperature, the control unit can adjust a value of the length of the storage life.

In an embodiment described above, the analytical device includes a plurality of first supply containers, especially 2 to 10 first supply containers, which contain the first reagent component. In such case, the analytical device can include one or more second supply containers, especially 2 to 10 second supply containers, which contain the second reagent component. For producing the reagent, the mixing apparatus supplies a predetermined amount of the second reagent component from the single supply container or from one of a number of second supply containers to one of the first supply containers, so that the first reagent component contained in the first supply container mixes with or dissolves in the second reagent component supplied to the first supply container.

Alternatively or supplementally to the monitoring of the time span since producing the most recently produced charge, the amount provided to the supply containers containing the first reagent component can be so dimensioned that the therewith produced charge suffices until the expiration of the length of the storage life at an average consumption rate of reagent by the analytical device.

In this embodiment, a value representing the consumption of the reagent and a value representing the amount of the first reagent component contained in the supply containers can be stored in a memory of the control unit. Based on these values, the control unit ascertains the time span after which a predetermined amount of the second reagent component is to be conveyed to a reagent container of the additional supply containers for producing a new reagent charge.

BRIEF DESCRIPTION OF THE DRAWINGS

The invention will now be explained in greater detail based on the examples of embodiments illustrated in the drawing, the figures of which show as follows.

DETAILED DESCRIPTION IN CONJUNCTION WITH THE DRAWINGS

Figure 1A:
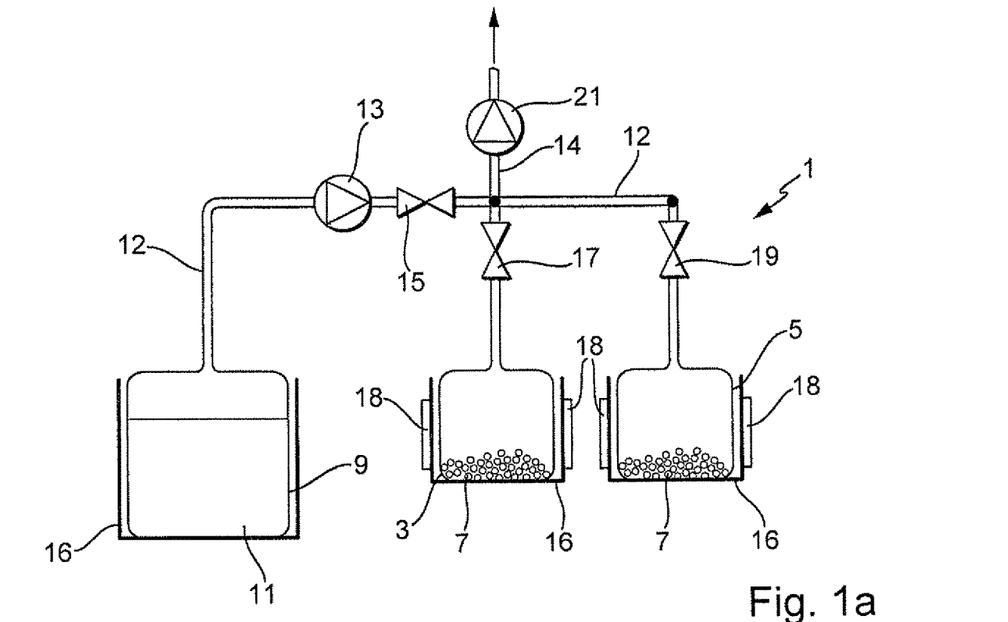
FIG. 1a) is a schematic representation of an arrangement of supply containers for reagent components and a mixing apparatus for producing a reagent charge according to a first embodiment.
Figure 1B:
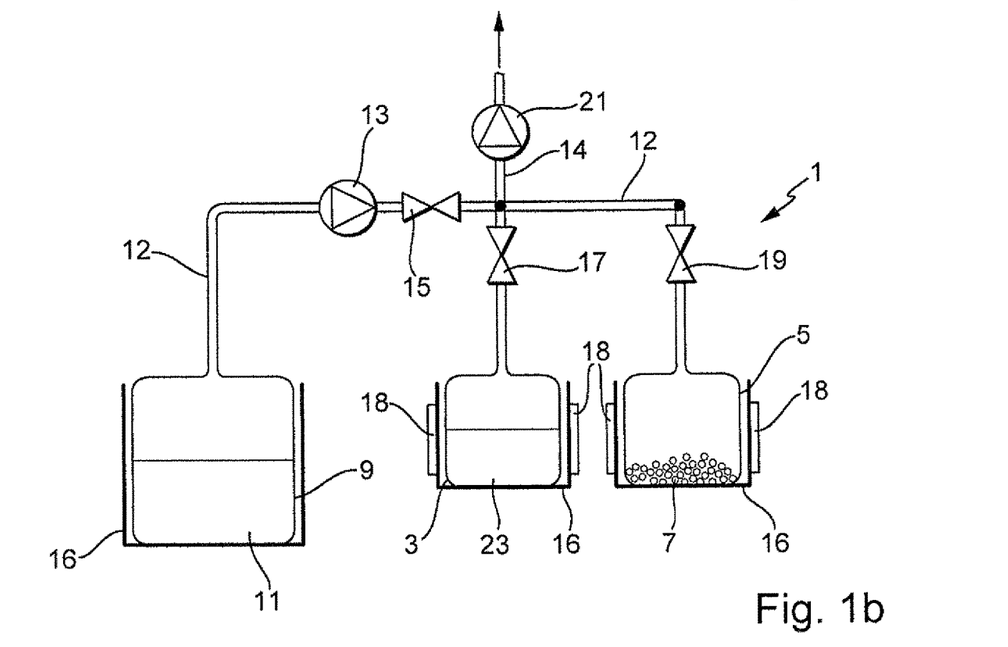
FIG. 1b) the arrangement after production of a first reagent charge.

An arrangement 1 of two first supply containers 3, 5 with a first reagent component 7 and a second supply container 9 with a second reagent component 11 is presented in FIGS. 1a) through d). In the example shown here first reagent component 7 is a solid, while second reagent component 11 is a liquid, in which first reagent component 7 is soluble.

Arrangement 1 can be part of an analytical device (not shown in FIG. 1), which serves to mix first reagent component 7 and second reagent component 11 with one another and so produce a charge of a predetermined amount of a reagent. This reagent can be used to treat a liquid sample in order to enable the determination of a measured variable of the liquid sample by the analytical device.

Second supply container 9 is connected to first supply containers 3 and 5 via a liquid line 12. A first supply system 13, for example, a peristaltic pump, syringe pump or membrane pump, serves to supply the second reagent component from second supply container 9 into liquid line 12 and via this to one of the first supply containers 3, 5. The liquid path from second supply container 9 to both first supply containers 3, 5 can be interrupted or opened by means of a valve 15. Moreover, additional valves 17, 19 are associated respectively with the first supply containers 3, 5; valves 17, 19 can block or permit the flow of liquid from liquid line 12 into the respective supply containers 3, 5. A liquid supply line 14 leaves liquid line 12 to feed a reagent supply line (not shown) of the analytical device. By means of an additional supply system 21, for example, a peristaltic pump, syringe pump or membrane pump, reagent 23 produced by mixing first reagent component 7 with second reagent component 11 can be conveyed into the reagent supply line via liquid supply line 14.

The measured variable to be determined by the analytical device can be, for example, a concentration of an analyte in the liquid sample. The determination of orthophosphate should serve as an example here. The method described here and in the following, however, can also be transferred to the determination of other measured variables, especially the determination of the concentrations of ammonium, nitrate, nitrite or silicate, chemical oxygen demand or water hardness. In determining orthophosphate using the ascorbic acid method according to EN-ISO 6878:2004, orthophosphate is treated with molybdate and antimony ions in an acid medium, whereby an antimony phosphorus molybdate complex forms. This is reduced to the intensively blue colored molybdenum blue complex with ascorbic acid. The concentration of orthophosphate in the liquid sample can be derived from a photometrically ascertained concentration of the molybdenum blue complex so formed. Further details are given in EN-ISO 6878:2004.

In EN-ISO 6878:2004, an ascorbic acid solution of 10±0.5 g ascorbic acid in 100±5 ml water is used. In an annotation, the standard indicates that the solution is storable in a brown glass bottle in the refrigerator for two weeks. Ascorbic acid is especially easily oxidized by air oxygen. If the analytical device should perform the determination of orthophosphate according to the standard, thus a regular renewing of the ascorbic acid solution to be used at time intervals of a few weeks is required. In previously known analytical devices, the renewing of the ascorbic acid solution is a maintenance measure to be performed by a service person.

By means of the arrangement shown in FIGS. 1 a) through d), maintenance free operation of the analytical device can be expanded from a few weeks up to a number of months. If the ascorbic acid is in its solid form, decomposition reactions, especially reactions with air oxygen, are significantly slower than in the case of aqueous ascorbic acid. The liquid reagent required for detection of orthophosphate, the aqueous ascorbic acid solution, can consequently be divided into two less reactive reagent components, namely into first reagent component 7, which comprises ascorbic acid as a solid, and into second reagent component 11, which comprises water serving as solvent. @In a similar manner, this can also be applied to reagents, which are used for the detection of other substances or for determining further measured variables in liquid samples. Fundamentally, the chemical substances, each of which contains the required reagent, can be divided into one or more reagent components, which are less reactive and therewith also less susceptible to decomposition reactions than the reagent to be produced from the reagent components. Fundamentally, it can especially be assumed therefrom that a solid reagent component is less susceptible to deterioration than the corresponding reagent component in solution. Furthermore, it can be taken into consideration with the separated provisioning of the reagent components described here, whether substances, which can react with one another, are contained in the reagent to be used in the analyzer.

Dividing the reagent into individual reagent components can correspondingly be performed in such a manner that such substances are stored as reagent components separated from one another, and so first come in contact with one another during producing the reagent by mixing the reagent components.

A control unit of the analytical device controls the automatic production of a charge of reagent, a charge of ascorbic acid solution in the example described here, by means of the arrangement shown in FIGS. 1 a) through d). For this, first valve 15 and valve 17 associated with first supply container 3 are opened, while supply system 13 supplies, from second supply container 9 to first supply container 3, an amount of second reagent component 11 corresponding to the amount of first reagent component 7 provided in accordance with a predetermined mixing ratio. First reagent component 7 provided as a granular material in supply container 3 dissolves in second reagent component 11 to form a reagent 23 for use in the analytical device; reagent 23 is an aqueous ascorbic acid solution in the example described here (FIG. 1b). In given cases, the mixing of the solution can be facilitated by a stirrer contained in supply container 3 or by recirculating the mixture. The amount of second reagent component 11 supplied is matched to the amount of first reagent component 7 provided in the first reagent container, so that the charge of reagent 23 produced has a standard concentration, here the concentration of ascorbic acid set forth above. For this, corresponding values are stored in the memory of a control unit (not shown in FIGS. 1 a) through d)) of the analytical device; the control unit drives supply system 13 in accordance with these stored values. The amount of first reagent component 11 applied for producing the charge of reagent 23, or the amount of second reagent component 11 remaining in second supply container 9 after production of the charge, can be stored in a memory area of a data memory associated with supply container 9. For example, this data memory can belong to the control unit of the analytical device. It can, however, also be a memory, which the control unit can access, arranged in another region of the analytical device. In this way, the control unit can monitor the fill level of supply container 9 or the consumption of second reagent component 11. The supply container, as described in DE 10 2009 029305 A1, for example, can be integrated in a removable cartridge. The data memory can be arranged in the cartridge in this case.

Figure 1C:
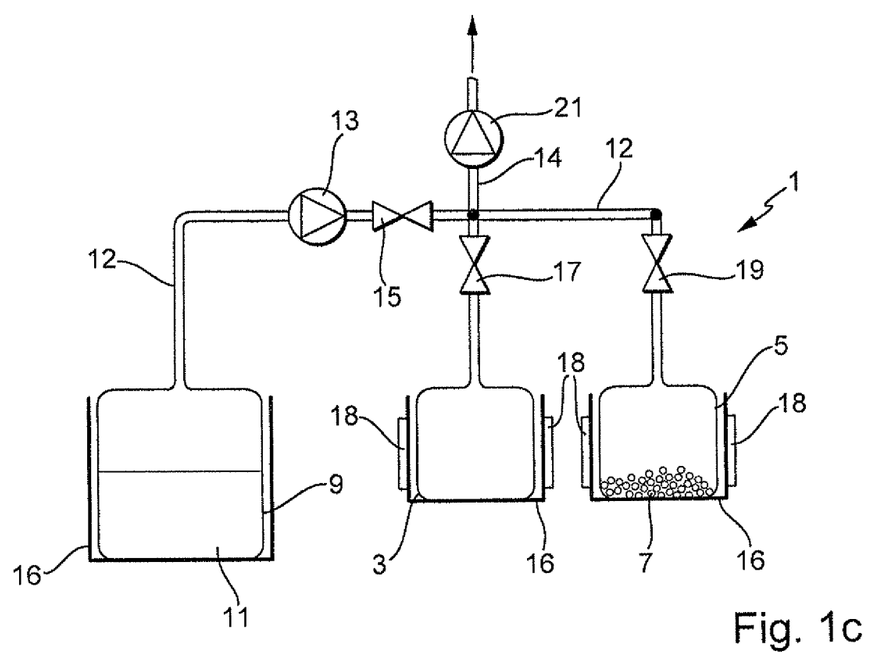
FIG. 1c) the arrangement after consumption of the first reagent charge.
Figure 1D:
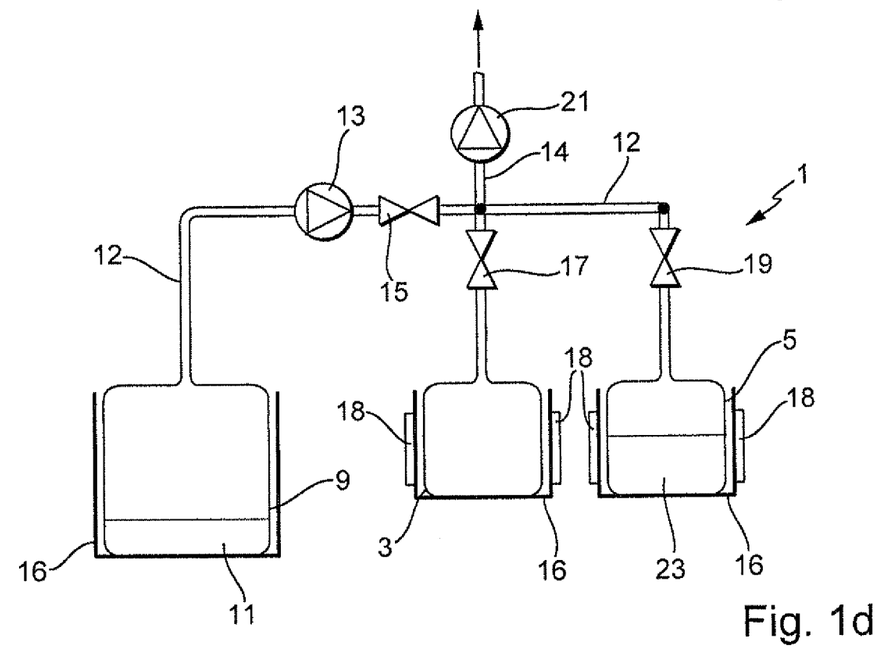
FIG. 1d) the arrangement after production of a second reagent charge.

In order to determine the measured variable, the orthophosphate concentration in the present example, in a liquid sample, the control unit supplies reagent 23 from first supply container 3 via liquid supply line 14 by means of the additional supply system 21 to a processing unit of the analytical device (not shown in FIGS. 1 a) through d)); the reagent is mixed with the liquid sample in the processing unit. For this, first valve 15 and valve 19 associated with the additional first supply container 7 are closed, while valve 17 associated with the first supply container containing reagent 23 remains open. The amount of reagent 23 produced according to FIG. 1b) is so dimensioned that it is used up at a predetermined reagent consumption rate by the analytical device within the length of the storage life of reagent 23 (FIG. 1c). The control unit of the analytical device can measure the passage of time since production of the charge of reagent 23 and in the case of reaching a length of the storage life stored in a data memory, the control unit stops the pumping of reagent 23 from the current charge. Even if reagent 23 should still be in the supply container 3 at this point in time, it is assured in this way that no reagent 23, whose length of the storage life is exceeded and correspondingly no longer assures a sufficient measurement quality, is conveyed into the processing unit for performing measurements. Alternatively or supplementally, an option is to store a value in the data memory associated with supply container 3, which contains the current charge of reagent 23; the value represents the amount of reagent currently contained in supply container 3. This value results from the amount of first reagent component 7 originally provided in first supply container 3 or from the amount of second reagent component 11 supplied from second supply container 9. The control unit can ascertain the amount of reagent 23 remaining in supply container 3 from the amount of reagent 23 supplied from supply container 3 by means of supply system 21 since producing the charge of reagent 23.

If the length of the storage life of reagent 23 has run out or supply container 3 is empty (FIG. 1c)), the control unit can produce a new charge of reagent 23. For this, it controls first supply system 13 and valves 15, 17, 19, in order to convey a predetermined amount of second reagent component 11 from second supply container 9 to the additional first supply container 5, so that the amount of first reagent component 7 provided therein dissolves in the supplied second reagent component 11 (FIG. 1d)). The provided or supplied amounts of the respective reagent components 7, 11 are dimensioned in the same manner as in producing the first charge (FIGS. 1a and b). The mixing also occurs in the same manner. After production of the new charge, then new reagent 23, in the present example a standard ascorbic acid solution, is available to determine the measured variable with a high quality of measurement. Supplying reagent 23 contained in the additional supply container 5 to the processing unit of the analytical device occurs by means of supply system 21 via liquid supply line 14 with a corresponding actuation of valves 15, 17, 19 of arrangement 1. The time passed since producing the new charge and/or the consumption of reagent 23 is monitored in the same manner as with the first charge of reagent 23.

Arrangement 1 can contain other first supply containers, in which a predetermined amount of first reagent component 7, especially the same amount of first reagent component 7, is provided to each supply container. The amount of second reagent component 11 contained in supply container 9 is so dimensioned that it is sufficient for producing a charge of reagent in all first supply containers present. It is also possible to divide the amount of second reagent component required into a number of second supply container.

The supply containers 9, 3 and 5 and, in given cases, other supply containers present, are embodied as reagent bags. In order to still further lengthen the storage life of the individual charges of reagent 23, at least those supply containers determined to contain reagent 23 can comprise a UV radiation and visible light impervious material, preferably supplementally an infrared radiation reflecting material. The reagent bags are held in support vessels 16. The side walls of support vessels 16 for the reagent bags, in which charges of reagent are produced and stored, are each coolable by means of a temperature regulating apparatus 18, which includes one or more Peltier elements, for example. A lessening of the rate, at which decomposition reactions of the reagent proceed, can be achieved through cooling, so that the length of the storage life can be lengthened further.

Since, after each consumption or after each expiration of the length of the storage life of a charge of reagent 23, a further charge of reagent is produced automatically, the analytical device can be operated maintenance free over a much longer period of time than known analytical devices, in which a new supply container must be made available by a maintenance technician after the expiration of the length of the storage life of the reagent.

Figure 2:
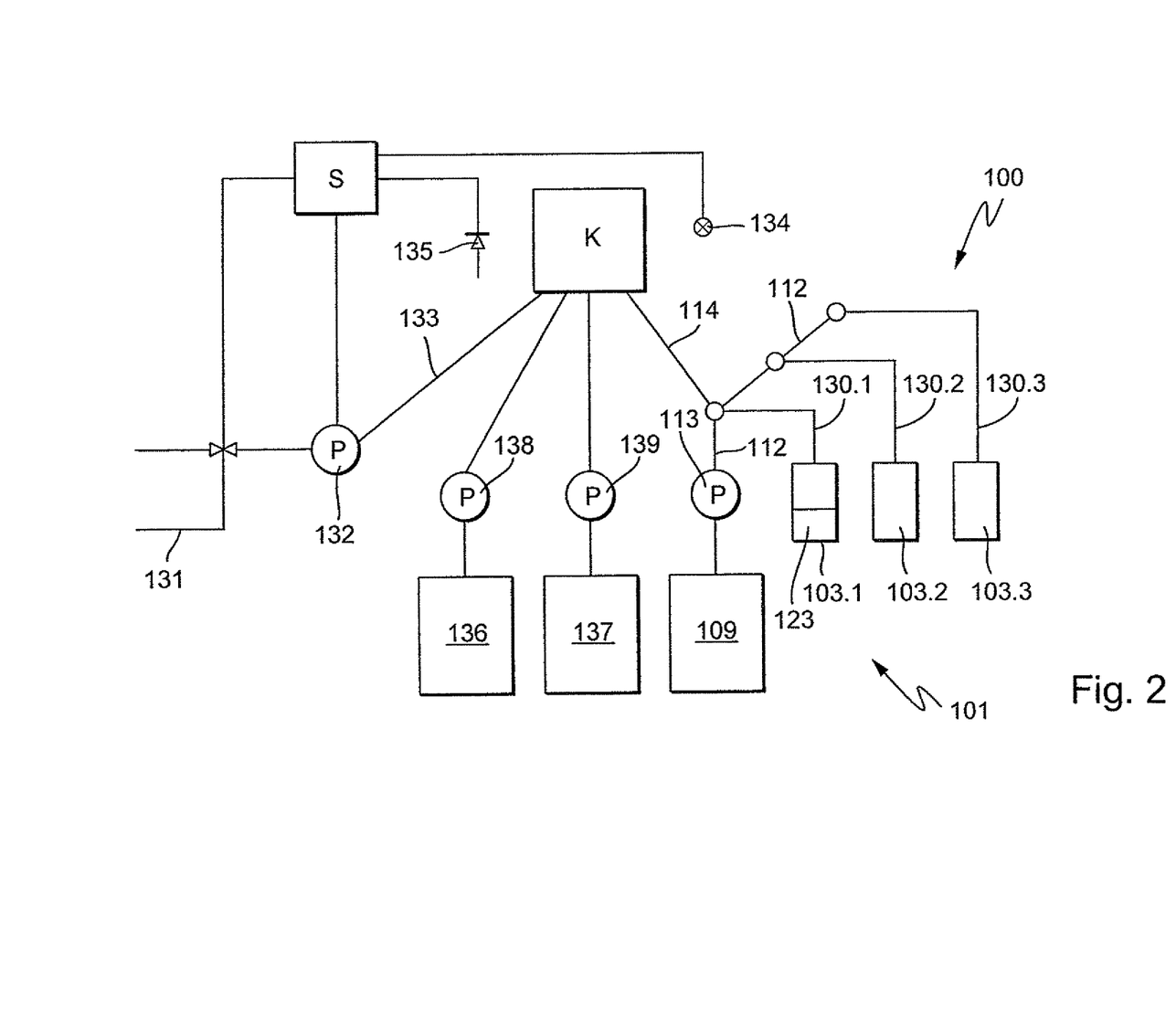
FIG. 2 is a schematic representation of an analytical device with an arrangement of supply containers for reagent components and a mixing apparatus for producing a number of reagent charges according a second embodiment.

FIG. 2 shows a schematic representation of an analytical device 100 having a number of supply containers 103.1, 103.2, 103.3, 109, 136, 137, a processing system with a number of supply systems 113, 132, 138, 139 for the liquids contained in supply containers 103.1, 103.2, 103.3, 109, 136, 137, liquid lines 112, 114, 130.1, 130.2, 130.3, 133, via which supply containers 103.1, 103.2, 103.3, 109, 136, 137 are connected to a mixing cuvette K. Mixing cuvette K serves both for the mixing of liquids supplied via liquid lines 112, 114, 130.1, 130.2, 130.3, 133 as well as a measuring cell for registering a measured value of the measured variable to be determined by means of the optical, especially photometric, measuring transducers 134, 135 of analytical device 100.

Analytical device 100 can be fully automated. For this, it possesses a control unit S, which, in the example shown here, also provides the functions of an evaluating unit, especially for determining a measured variable based on a measured value registered by the measuring transducer. Control unit S includes a data processing system, for example, a computer or a measurement transmitter, having at least one processor and one or more data memories. Control unit S can also have an input apparatus for the input of commands or parameters by a service person and/or an interface for the receipt of commands, parameters or other data from a superordinated unit, for example, a process control system. Furthermore, the control unit can also have an output apparatus for the output of data, especially measurement results or operating information, to a user or have an interface for the output of data to the superordinated unit. Control unit S is connected to drivers for the supply systems 113, 132, 138, 139 and with valves (not illustrated in detail here) in order to convey liquids from supply containers 103.1, 103.2, 103.3, 109, 137, 136 to mixing cuvette K or out from mixing cuvette K and to create one or more charges of reagent 123. Pumps, especially membrane pumps, hose pumps or peristaltic pumps and/or syringe pumps are possible supply systems, for example. Moreover, control unit S is connected to the measuring transducer, which includes an optical transmitter 134 and an optical receiver 135 in the example shown here, in order to control these and to ascertain the measured variable to be determined from measurement signals of receiver 135. The analytical device can also have other data memories associated with the liquid containers; referenced data, such e.g. consumption, length of storage life or fill level are stored in these memories. The control unit can have read and/or write access to these data memories.

Analytical device 100 includes an arrangement 101 of supply containers 109, 103.1, 103.2, 103.3 connected to one another via liquid lines 112, 130.1, 130.2, 130.3; supply containers 109, 103.1, 103.2, 103.3 are embodied in a manner analogous to those described for FIG. 1a) through d) to produce, one after the other, a number of reagent charges from a first reagent component provided in a plurality of first supply containers 103.1, 103.2, 103.3 and a second reagent component contained in second supply container 109. Producing the reagent charges is automatically performed by control unit S. The liquid lines 112, 130.1, 130.2, 130.3 connected to supply containers 109, 103.1, 103.2, 103.3, supply system 113, which serves to convey liquid from the second supply container 109 to each first supply container 103.1, 103.2, 103.3, and valves not shown in greater detail, which serve to open or block the liquid paths connected to supply containers 109, 103.1, 103.2, 103.3, form a mixing apparatus for the production the reagent charges. Control unit S is embodied to actuate the drives (not shown) of supply system 13, which, for example, can be embodied as a syringe pump, and the individual valves, especially for mixing the reagent components for producing one or more reagent charges.

As before, the second reagent component is also a liquid in the example of FIG. 2. The first reagent component can be either liquid or solid. By dosing a predetermined amount of the liquid second reagent component contained in the second supply container 109 into one of the first reagent containers 103.1, 103.2, 103.3, a charge of a reagent to be used for treating a liquid sample in analytical device 100 can be produced. Therewith, three automatically produced reagent charges are available one after the other to analytical device 100. The time span, within which the analytical device can be operated without the exchange of supply containers by operators and without interruption, is practically tripled in this way, wherein, however, it is to be taken into consideration that the separately stored, reagent components have, in given cases, a limited length of the storage life. When required, still more first supply containers can be provided so that correspondingly more automatically produced reagent charges can be made available. If a number of reagents with limited storage life are required by the analytical device to determine the measured variable, a number of arrangements corresponding to arrangement 101, each including a number of supply containers and a mixing apparatus for producing a number of charges of each different reagent, can be provided.

Arrangement 101 functions in a manner analogous to arrangement 1 as described in FIGS. 1a) through d). Supply system 13 can be embodied as a syringe pump, for example. In a first step, a certain amount of the second reagent component can be conveyed from second supply container 109 to the cylinder of the syringe pump by the control unit controlling the actuation of the syringe pump. In a second step, the liquid can be conveyed from the cylinder to one of first supply containers 103.1 through a corresponding control of the syringe pump actuation and the valves of arrangement 101. The mixture formed in supply container 103.1 can be recirculated for a better mixing of the two reagent components and to support the dissolution of the first reagent component in the second reagent component. In such case, the mixture is first conveyed back into the cylinder of the syringe pump by a corresponding actuation of the syringe pump driver and the valves of arrangement 101 and then transported back into the supply container 103.1. When required, this can be repeated until reagent 123 is formed by the complete dissolution of the first reagent component in the second reagent component.

First supply container 103.1 serves as a reagent reservoir for a time span, which corresponds to a maximum length of the storage life of the reagent stored in the control unit; for determining the measured variable, the control unit supplies a predetermined amount of reagent from first supply container 103.1 into mixing cuvette K of analytical device 100, in order to mix such reagent with liquid sample. For this purpose, control unit S actuates the valves of arrangement 101 so that a liquid path from supply container 103.1, which contains reagent 123, to syringe pump 113 is opened. Moreover, control unit S actuates the driver of syringe pump 113, in such a manner that the amount of the reagent required for a measurement is conveyed to the piston of syringe pump 113. Then, the valves of arrangement 101 are actuated so that a liquid path is opened via a liquid line 114 between the syringe pump 113 and the mixing cuvette K. By actuating syringe pump 113, reagent 123 is conveyed into the mixing cuvette via liquid line 114.

@The analytical device 100 furthermore includes a liquid supply line 131 for supplying liquid sample from a sample supply (not shown). Liquid supply line 131 for the liquid sample is connected to mixing cuvette K via another liquid line 133. Control unit S supplies the liquid sample into the mixing cuvette by means of the supply system 132, which can be embodied, for example, as a syringe pump, for treatment by adding reagent 123. Thus, fed to the cuvette are the liquid sample, as described previously, the reagent 123 from supply container 103.1 and, in given cases, other reagents from, in given cases, additional supply containers (not shown here) of analytical device 100.

Mixing cuvette K simultaneously serves as a measuring cell in the example shown here. It can comprise, for example, a material transparent to the measuring radiation transmitted by the optical transmitter 135 of the photometric measuring transducer. If, for example, visible light or UV radiation serves as the measuring radiation, the material for the mixing cuvette can comprise, for example, quartz glass. Mixing cuvette K can also have optical windows, which transmit the measuring radiation.

In a modified embodiment of the analytical device, the mixing cuvette can also be placed upstream from an actual measuring cell. After treatment of the liquid sample in the mixing cuvette, the treated liquid sample is, in this case, then forwarded to the measuring cell, where a measuring transducer is brought into contact with the treated liquid sample provided in the measuring cell, in order to register measured values correlated with the measured variable to be determined.

In the present example, the radiation transmitted through the measuring cell and therewith through the treated liquid sample is received by receiver 134, which outputs a measurement signal to control unit S correlating with the intensity of the transmitted radiation. Control unit 8 is embodied to derive from the measurement signal a measured value of the measured variable to be determined and to store the measured value and/or output the measured value to a user interface.

After determining the measured variable, measuring cell 131 is emptied. Furthermore, analytical device 100 has other supply containers 136, 137 available, which can contain standard solutions for calibrations and/or cleaning solutions. By means of the supply systems 138, 139 associated with supply containers 136, 137, together with the appropriate valves of the processing system, these solutions can be conveyed to mixing cuvette K.

After one or more measuring cycles are performed, a calibration of the analytical device can be performed by conveying a calibration standard from supply container 136 to mixing cuvette K. The calibration standard is treated with reagent 123, as a "real" liquid sample from the sample supply would be, in the mixing cuvette; reagent 123 is dosed from the supply container 103.1 into the mixing cuvette via liquid line 114. A measured value of the measured variable is determined photometrically by measuring transducers 134, 135 and, if needed, an adjustment of analytical device 100 is performed based on the measured value known for the calibration standard.

As already described in the example in FIGS. 1a) through d), the control unit S of analytical device 100 illustrated in FIG. 2 also monitors the amount of reagent 123 used in measurement operation and/or the time, which has passed since production of the current reagent charge. In the case of a complete consumption of the reagent or an expiration of the length of the storage life stored in the control unit, the control unit produces anew an additional reagent charge by conveying the second reagent component from the second supply container to an additional supply container 103.1, in which the first reagent component is provided.

The point in time at which the length of the storage life of a current reagent charge is reached or exceeded can also be detected by a sensor. For this, a calibration measurement can be advantageously utilized, since a standard solution is applied in the calibration; in contrast to a liquid sample removed from the sample supply, the standard solution is reliably free of additional influences, such e.g. turbidity or discoloration. Consequently, during calibration measurements, an additional measured value can be registered, which represents the degree of deterioration of the reagent. In the example of orthophosphate detection mentioned above, an aqueous ascorbic acid solution is used as a reagent. A yellow/brown discoloration of the solution occurs with the aging of the ascorbic acid solution. The progress of this discoloration is a measure for the progress of the decomposition reactions of the ascorbic acid. In addition to or instead of monitoring the time that has passed since producing the current reagent charge, or monitoring the reagent consumption, the discoloration can be taken into consideration for monitoring the aging of the reagent with a sensor. Thus, for example, a photometric measurement using a wavelength of 400 nm can be performed for monitoring the ascorbic acid solution for the orthophosphate determination during calibration. The absorption of this wavelength serves as a measure for the progress of the decomposition of the ascorbic acid. A threshold value of the absorption corresponding to a state, in which reliable analytical results can still be achieved, of the ascorbic acid solution to be monitored can be stored in a memory of control unit S. If this value is reached or exceeded, the length of the storage life of the reagent has also been exceeded. Control unit S then no longer accesses the current reagent charge, but instead produces a new reagent charge, as described.

In order to increase the length of the storage life of the reagent, the analytical device can have a temperature regulating apparatus for first supply containers 103.1, 103.2, 103.3; at least the supply container containing the current reagent charge can be cooled by means of the temperature regulating apparatus. Supply containers 109, 103.1, 103.2, 103.3, 136, 137 can be embodied as a reagent bag in the same manner as the example described based on FIGS. 1a) through d).

The invention claimed is:

1. An analytical device for automated determination of a measured variable of a liquid sample, comprising:
   a measuring cell;
   a sample pump configured to convey the liquid sample through a flowpath from a sample supply to the measuring cell;
   a reagent reservoir in communication with the measuring cell via a reagent supply line;
   a plurality of first supply containers containing a first reagent component, wherein one of the plurality of first supply containers is a reagent reservoir in communication with the measuring cell via a reagent supply line;
   at least one second supply container containing a second reagent component, wherein the second reagent component is a liquid, and the first reagent component is a solid that is soluble in the second reagent component;
   a mixing pump and associated valves configured to produce a charge of a desired reagent in the reagent reservoir by conveying a predetermined amount of the second reagent component from the at least one second supply container to the reagent reservoir and mixing the predetermined amount of the second reagent component with the first reagent component from one of the first supply containers, and further configured to convey the charge of the desired reagent through the reagent supply line to the measuring cell to yield a treated liquid sample therein;

a measuring transducer for registering a measured value of the treated liquid sample contained in said measuring cell, the measured value correlated with the measured variable;

an evaluating unit, including a processor and data memory, configured to determine the measured variable based on the measured value registered by said measuring transducer; and a control unit configured to command the sample pump and the mixing pump and associated valves.

2. The analytical device of claim 1, further comprising a mixing cell disposed upstream of the measuring cell and in communication with the sample supply and the reagent reservoir such that the liquid sample conveyed by the sample pump and the charge of the desired reagent conveyed by the mixing pump are conveyed to the measuring cell via the mixing cell.

3. The analytical device as claimed in claim 1, further comprising liquid supply lines connecting said at least one second supply container to said plurality of first supply containers.

4. The analytical device as claimed in claim 1, wherein a first value representing a length of a storage life of the desired reagent is stored in a memory of said control unit, and said control unit is embodied to ascertain a time span, after which a new charge of the desired reagent is to be produced based on the first value.

5. The analytical device as claimed in claim 1, wherein said first supply containers contain a predetermined amount of the first reagent component, which is selected such that the charge of the desired reagent obtained by mixing the predetermined amount of the first reagent component with the second reagent component is consumed within a predetermined length of the storage life of the desired reagent given a predetermined consumption of the desired reagent by the analytical device.

6. The analytical device as claimed in claim 1, wherein the first reagent component is a powder or granular material that is soluble in the second reagent component.

7. The analytical device as claimed in claim 1, wherein said first supply containers and the at least one second supply container are embodied as flexible reagent bags, each connected to a liquid line of the analytical device.

8. The analytical device as claimed in claim 1, further comprising a temperature regulator in thermal communication with at least one of said first supply containers, wherein said temperature regulator includes a thermoelectric device.

9. The analytical device as claimed in claim 8, wherein the temperature regulator is a Peltier element.

10. The analytical device as claimed in claim 1, further comprising a removable cartridge, wherein said first supply containers and said at least one second supply container are arranged in said removable cartridge of the analytical device, said removable cartridge including a temperature regulator structured to regulate the temperature of at least one or all supply containers.

11. The analytical device as claimed in claim 1, wherein:
a first value representing consumption of the desired reagent during operation of the analytical device and a second value representing the amount of the first reagent component contained in said first supply containers are stored in a memory of said control unit, and said control unit is embodied to ascertain a time span, after which a new charge of desired reagent is to be produced, based on the first and second values.

12. The analytical device as claimed in claim 1, wherein:
a first value representing the length of the storage life of the desired reagent and a second value representing consumption of the desired reagent during operation of the analytical device and a third value representing the amount of the first reagent component contained in said first supply containers are stored in a memory of said control unit, and said control unit is embodied to ascertain a time span, after which a new charge of desired reagent is to be produced, based on the first value or on the second and third values.

13. A method for monitoring a measured variable in a liquid to be monitored using an analytical device including a processing system controlled by a control unit, a measuring cell, a measuring transducer and an evaluating unit, comprising the steps of:

producing at least one desired reagent using the processing system of the analytic device;

treating a liquid sample of the liquid to be monitored using the processing system, wherein the treating includes adding the at least one desired reagent to the liquid sample to yield a treated liquid sample;

supplying the treated liquid sample to the measuring cell;

registering, using the measuring transducer, a measured value correlated with the measured variable of the treated liquid sample supplied to the measuring cell and transmitting the measured value to the evaluating unit; and determining by the evaluating unit a value of the measured variable based on the measured value registered by the measuring transducer, wherein the processing system includes a plurality of first supply containers containing a predetermined amount of a first reagent component, at least one second supply container containing a second reagent component, and a mixing pump in communication with the plurality of first supply containers and the at least one second supply container via a supply line, wherein the second reagent component is a liquid and the first reagent component is a solid, which is soluble in the second reagent component, and wherein, for producing the at least one desired reagent, the control unit commands the mixing pump to supply a predetermined amount of the second reagent component from the at least one second supply container to one of the first supply containers through the supply line such that the first reagent component contained in the first supply container dissolves in the second reagent component.

14. The method as claimed in claim 13, wherein a measuring cycle of the analytical device includes said steps of:

treating the liquid sample;
supplying the treated liquid sample to the measuring cell;
registering and transmitting the measured value correlated with the measured variable; and
determining the value of the measured variable based on the measured value, wherein the producing of the at least one desired reagent yields a charge of the desired reagent in an amount sufficient for performing a plurality of measuring cycles.

15. The method as claimed in claim 14, wherein the charge of desired reagent is held in a supply container serving as a reagent reservoir, and the processing system supplies desired reagent from the reagent reservoir to the liquid sample.

16. The method as claimed in claim 14, wherein the control unit, after consumption of a most recently produced charge of desired reagent or after the expiration of a storage life of the most recently produced charge of desired reagent, commands the processing system to produce a new charge of desired reagent by mixing a predetermined amount of the first reagent component with a predetermined amount of the second reagent component.

17. The method as claimed in claim 16, wherein expiration of the storage life is detected by means of a sensor.

18. The method as claimed in claim 13, wherein the analytical device comprises 2 to 10 first supply containers and 2 to 10 second supply containers.

\* \* \* \* \*